(12) United States Patent
Dale (10) Patent No.: US 8,722,392 B2
(45) Date of Patent: May 13, 2014

(54) LIVESTOCK FEED FROM CORN ETHANOL BYPRODUCT

(75) Inventor: Ross Dean Dale, Pella, IA (US)

(73) Assignee: Golden Corn Technologies, L.L.C., Oskaloosa, IA (US)

(*) Notice: Subject to any disclaimer, the term of this patent is extended or adjusted under 35 U.S.C. 154(b) by 0 days.

(21) Appl. No.: 13/433,099

(22) Filed: Mar. 28, 2012

(65) Prior Publication Data

US 2012/0183643 A1 Jul. 19, 2012

Related U.S. Application Data

(63) Continuation-in-part of application No. 12/399,716, filed on Mar. 6, 2009, now Pat. No. 8,173,412.

(60) Provisional application No. 61/490,956, filed on May 27, 2011.

(51) Int. Cl.
*C11C 1/00* (2006.01)

(52) U.S. Cl.
USPC .......................................................... 435/271

(58) Field of Classification Search
None
See application file for complete search history.

(56) References Cited

U.S. PATENT DOCUMENTS

| | | | |
|---|---|---|---|
| 5,503,750 A | 4/1996 | Russo | |
| 5,863,574 A | 1/1999 | Julien | |
| 6,660,506 B2 | 12/2003 | Nguyen et al. | |
| 6,962,722 B2 | 11/2005 | Dawley et al. | |
| 7,255,873 B2 | 8/2007 | Nakata | |
| 7,263,934 B2 | 9/2007 | Copeland et al. | |
| 7,309,602 B2 | 12/2007 | David | |
| 7,527,941 B1 | 5/2009 | Hogen et al. | |
| 7,601,858 B2 | 10/2009 | Cantrell et al. | |
| 7,608,729 B2 | 10/2009 | Winsness et al. | |
| 8,008,516 B2 | 8/2011 | Cantrell | |
| 8,008,517 B2 | 8/2011 | Cantrell | |
| 8,143,444 B2 | 3/2012 | Mariansky | |
| 8,153,006 B1 | 4/2012 | Fessler | |
| 8,283,484 B2 | 10/2012 | Cantrell | |
| 2003/0232109 A1 | 12/2003 | Dawley | |
| 2004/0023349 A1 | 2/2004 | Bisgaard-Frantzen et al. | |
| 2006/0041153 A1 | 2/2006 | Cantrell et al. | |
| 2006/0251764 A1 | 11/2006 | Abbas et al. | |
| 2007/0036881 A1 | 2/2007 | Griffith | |
| 2007/0128334 A1 | 6/2007 | Pittman | |
| 2007/0210007 A1 | 9/2007 | Scheimann et al. | |
| 2007/0231311 A1 | 10/2007 | Kroening | |
| 2007/0238891 A1 | 10/2007 | Winsness et al. | |
| 2007/0249029 A1 | 10/2007 | Marshall et al. | |
| 2008/0003654 A1 | 1/2008 | Hirl | |
| 2009/0006280 A1 | 1/2009 | David | |
| 2011/0008489 A1 | 1/2011 | Robb et al. | |
| 2011/0223284 A1 | 9/2011 | David | |
| 2011/0269185 A1 | 11/2011 | David | |
| 2012/0208252 A1 | 8/2012 | Brotherson | |
| 2012/0244591 A1 | 9/2012 | Brotherson | |
| 2013/0149750 A1 | 6/2013 | Brotherson | |
| 2013/0149763 A1 | 6/2013 | Brotherson | |
| 2013/0149764 A1 | 6/2013 | Brotherson | |

FOREIGN PATENT DOCUMENTS

| | | |
|---|---|---|
| WO | WO 92/15771 A1 | 9/1992 |
| WO | WO 02/38786 A1 | 5/2002 |
| WO | WO 2005/079190 A2 | 9/2005 |
| WO | WO 2005/079193 A2 | 9/2005 |
| WO | WO 2006/023432 A2 | 3/2006 |
| WO | WO 2007/056321 A1 | 5/2007 |
| WO | WO 2007/098396 A2 | 8/2007 |

OTHER PUBLICATIONS

Zhang et al "Increased Production of alpha-Amylase by *Bacillys amloliquefaciens* in the Presence of Glycine" Applied and Environmental Microbiology 1983 vol. 46 No. 1 pp. 296-295.
PCT/US07/66024, Oct. 25, 2007, David.
Direvo Industrial Biotechnology, GMBH, "Direvo reaches milestone in consolidated bioprocessing of lignocellulose to lactic acid," Press Release dated Mar. 11, 2013.
"BluCon-L," printed May 13, 2013, from Internet website found at http://www.direvo.com/processes/blucon-l.html.
"Technology Platform," printed May 13, 2013, from Internet website found at http://www.direvo.com/processes/platform.html.
International Search Report and Written Opinion of the International Searching Authority, PCT/US2012/036526, dated Oct. 24, 2012.

*Primary Examiner* — Suzanne M Noakes
(74) *Attorney, Agent, or Firm* — Boardman & Clark LLP (57) ABSTRACT

A method for processing of byproducts in an ethanol production process to improve their nutritional value is provided. The method includes applying a mixture of microorganism to a stillage stream with concomitant production of organic acids and de-emulsification and liberation of oil for recovery. An improved livestock feed resulting from ethanol production is provided which comprises a much reduced oil content and a much higher level of organic acids.

19 Claims, 2 Drawing Sheets

LIVESTOCK FEED FROM CORN ETHANOL BYPRODUCT

CROSS-REFERENCE TO RELATED APPLICATIONS

This application claims the benefit of U.S. Provisional Application, Ser. No. 61/490,956 entitled "Improved Livestock Feed From Corn Ethanol Byproduct" filed on May 27, 2011, and this application is a Continuation-in-Part of and claims priority to U.S. patent application Ser. No. 12/399,716, entitled "Method of Liberating Bound Oil Present in Stillage" filed on Mar. 6, 2009, the entire contents of each of which is hereby incorporated by reference herein in its entirety.

FIELD

This invention is generally directed to methods of improving the nutritional value of ethanol distillers grains and solubles byproducts.

BACKGROUND

The production of ethyl alcohol in dry-mill ethanol plants utilizing grains as feedstock is a major fuel alcohol in the U.S.A. A plant utilizing corn as feedstock can typically produce 2.7-2.8 gallons of ethanol and 17-18 lbs. of distillers grains with solubles (dry basis) per bushel of corn. While ethanol is the core product and the reason the processing plant exists, the byproduct, distillers grains with solubles, is also an important and significant revenue stream for an ethanol plant. Beyond increasing or improving the efficiency ethanol production and yield from corn, optimizing the value and dollar return of the byproduct stream is critically important to maximize profitability.

However, the dramatic increase in ethanol production from corn since 1999 has led to a faster growth in distillers grains supply compared with demand. The over-supply compared with demand has caused a reduction in price of distillers grains equal to 50% when expressed on a corn equivalent basis. That is, distillers grains sold for 1.2 times the price of corn ten years ago but now sell for 0.7 times the price of corn.

One proposed method of increasing the demand of the byproduct is to remove the crude oil contained within it for use in other industrial processes such as biodiesel production. A lower oil ethanol byproduct could be used at higher inclusion levels in livestock diets. Each bushel of corn that may produce 2.7 gallons of ethanol, also contains approximately 2 lbs. of corn oil. Further, a typical 100 million gallon per year corn-to-ethanol plant will discard approximately 40,000 short tons of crude corn oil per year in the distillers grains byproduct. When distillers grains are used as feed, at higher levels of inclusion of the byproduct the oil content in the byproduct begins to have deleterious effects on the animal, such as reduced milk fat production in dairy cows, reduced conception rates, soft fat in pork and bacon due to a high level of unsaturation, as well as reduced feed intake and weight gain in beef feedlot cattle. Therefore, there are significant advantages to removing the oil from the byproduct, such as increasing the level of effective inclusion in livestock diets and allowing the oil to be directed toward higher value industrial processes or feed markets.

However, when a significant amount of oil is removed from distillers grains, the digestible energy content of the feedstuff is also reduced as oil contains 2.25× the gross energy compared with carbohydrates. This results in a distillers grains feedstuff that may be used at higher inclusion levels but has a much reduced digestible energy content compared with the full oil distillers grains.

Solutions have been attempted to remove oil from grains. For example, soybeans, canola, sunflowers, cottonseed, peanuts, and other commodities are valued for their oils. Technologies, such as solvent extraction or extrusion, exist for the efficient and economical removal of oil from these commodities. However, these same technologies are generally applied to corn at the front end of an ethanol production process, that is, prior to distillation. Unfortunately, the oil content in corn grain is typically only between 3.5% and 4.0% and removing it from the grain is not very cost effective. An alternative solution is to fractionate the germ from the rest of the corn kernel for oil removal, as the germ contains approximately 25% oil. It is by this fractionation method that commercial corn oil is typically obtained in the wet milling industry. Unfortunately, in dry milling, corn components such as germ, pericarp and endosperm do not separate easily or cleanly, as compared to wet milling processes. For example, the germ can be separated by a dry milling process, however it is at the expense of some starch loss which results in lower ethanol plant productivity and profit.

In addition to the current issues in removing oil, in the ethanol production process, thin stillage typically can only be condensed to a total solids content ranging between 20% and 30%. Further, the gums and waxes in the thin stillage cause the solubles to become very viscous when it is condensed and these components often cause fouling of condensers. Further, while it is possible to use a high speed centrifuge to remove crude corn oil from thin stillage, the industry has only been able to achieve between 25%-80% removal of total oil in thin stillage due to the presence of these gums and waxes which are bound with the oil and are loathe to relinquish their bonds. At best, solutions to remove or separate crude oil in thin stillage necessitate the use of very high speed, costly centrifuges to recover a portion of the oil as the gums within stillage bind the oil. Moreover, the 25%-80% recovery of total oil in thin stillage is equal to only approximately 32% of the total oil available in whole stillage (40% of the oil from whole stillage present in thin stillage multiplied by 80% recovery).

Separation of oil from the grains, which constitutes a majority of the oil, cannot typically be accomplished by centrifugation because the oil is still bound within the germ. Therefore, solutions often include extraction methods. Typical extraction methods for oilseeds include solvent extraction with organic solvents such as hexane, benzene, ethanol, methanol and others, as well as extruding techniques which apply very high pressure and temperature to the material to 'squeeze' the oil out. Unfortunately, these methods are high cost compared with the relatively low amount of oil contained within the distillers grains (about 7.5% on a dry basis) and often include toxic chemicals. In addition, solvent extraction is not oil-specific but also extracts other components soluble in organic solvents, such as the gums which are also present in thin stillage, resulting in a crude oil with a high level of impurities requiring further refining.

Accordingly, there is a need in the art to produce a distillers grains ethanol coproduct that can be used at higher inclusion rates in livestock diets without reducing animal production or performance and that has significantly reduced oil content and increased digestible energy.

Further, there is a need in the art to more efficiently extract and reduce the oil content of distillers grains byproduct in a dry mill ethanol plant.

Further, there is also a need to increase the digestible energy content and nutritional value of distillers grains.

Further, there is a need in the art to produce a distillers grains byproduct with reduced oil content.

Further, there is a need in the art to produce a distillers grains product that can be fed at higher inclusion levels in livestock diets, thereby replacing more corn.

SUMMARY

A method for processing waste streams in an ethanol production process to produce an improved livestock feed is provided. The method includes applying a mixture of a microorganism and an enzyme to a stillage stream, fermenting carbohydrates into organic acids while also metabolizing gums and proteins in the stillage stream using the mixture to release oil in the gums and proteins carried by the stillage stream and recovering the oil.

A method of liberating bound oil present in stillage is also provided. The method comprises applying a microorganism to whole stillage to metabolize the stillage and separate oil bound to gums within the stillage, the microorganism further producing a byproduct comprising an enzyme adapted to metabolize at least one of a protein and a polysaccharide in the stillage.

A further method of releasing bound oil in stillage is provided. The method includes propagating a microorganism in stillage which utilizes gums present in stillage as a source of metabolizable carbohydrate. The method also includes providing an enzyme to the stillage which acts extracellularly to hydrolyze at least one of a protein and a polysaccharide in the stillage. These steps result in releasing oil from the gums and the at least one protein and polysaccharide to form free oil from an emulsion within the stillage.

A method of increasing the digestible energy of reduced oil distillers grains is provided. The method includes propagating a microorganism in stillage which ferments carbohydrates, proteins and polysaccharides into short chain organic acids.

A method of increasing the optimal inclusion level of distillers grains into livestock diets is provided. The method includes propagating a microorganism in stillage that results in significant oil liberation followed by separation along with significant production of nutrient dense organic acids.

BRIEF DESCRIPTION OF THE DRAWINGS

Various examples of embodiments of the systems, methods, and products according to the present disclosure will be described in detail, with reference to the following figures, wherein.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

As described herein, the feeding value and usefulness of ethanol byproduct stillage or distillers grains is improved during a fermentation process, such as may occur during an ethanol production process. The method generally includes fermentation of a stillage stream to convert carbohydrates into energy dense organic acids while concomitantly metabolizing components within stillage which form emulsions, thereby liberating oil for recovery. The process is implemented at or near the "end" of the ethanol production process, and more preferably after the distillation step. Oil is extracted from the whole stillage or thin stillage. While the process described herein is particularly adapted to corn processing and production of ethanol and corresponding byproducts, it is contemplated that the process or components thereof may be applied more generally to a fermentation process and/or may be fitted or arranged for application to products such as soybeans, canola, sunflowers, cottonseed, peanuts, or other commodities where said commodities are compatible for use with the methods and material described herein, and their processing without departing from the overall scope of the present invention.

Figure 1:
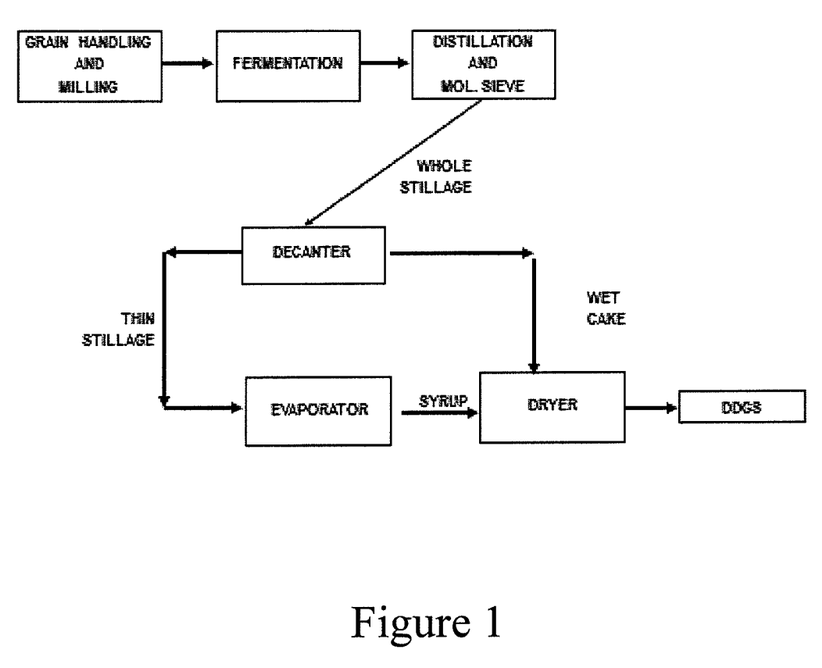
FIG. 1 shows a schematic diagram of a process flow in a dry mill ethanol plant suitable for use with the method of liberating bound oil described herein.

FIG. 1 illustrates one or more examples of a process flow in a dry mill ethanol plant. In the production of ethanol, generally, corn is ground and formed into a slurry. The slurry is mixed and formed into a liquid or liquefaction. The liquid is then fermented to form the mash or beer, and subsequently distilled. That is, ethyl alcohol is distilled off of the corn based product stream, which is generally in the form of a mash or beer separating the product stream into ethanol and whole stillage. After the ethyl alcohol is distilled off of the mash or beer, whole stillage is the remaining fermentation media containing remaining nutrients, including corn oil. The grains or large insoluble fractions may be removed from the whole stillage by centrifugation or filter presses.

Two byproduct streams result from the foregoing process; a first stream including large particle, insoluble distillers grains and a second stream of a thin syrup or stillage containing the solubles and small insoluble components that are not easily separated into the grains fraction. The thin stillage generally includes dissolved solubles in water along with the small insoluble components.

As a non-limiting example, one ton of whole stillage may contain 15% total solids, 1.6% corn oil, 1.5-3.0% ethanol soluble carbohydrates, and less than 0.5% organic acids by weight.

The oil may include one or more of triglycerides, diglycerides, monoglycerides and free fatty acids. The bound oil in the whole or thin stillage may be bound in compounds within stillage such as, but not limited to, glycolipids, phospholipids, glycosphingolipids, plant waxes, glycerophospholipids and lipidproteins. This group of compounds is referred to herein as "gums". The oil is emulsified or bound with the gum. The bound oil is generally in the non-aqueous phase.

The ethanol soluble carbohydrates may include one or more of sucrose, glucose, fructose, maltose, mannose, maltose, xylose, raffinose, and their equivalents.

The organic acids may include one or more of lactic, acetic, propionic, butyric, iso-butyric, valeric, iso-valeric, succinic, citric, malic, fumaric, aspartic and others or their equivalents.

Microorganisms, enzymes or any combination thereof are added to the stillage, namely the whole or thin stillage, to metabolize the oil containing compounds within whole or thin stillage, causing the oil to become unbound, thereby making it easier to recover the oil by conventional means. Concomitantly, carbohydrates in the stillage are also metabolized or digested by the microbes to produce organic acids, thereby increasing the digestible energy of the final feedstuff. To this end, a concentration of microorganisms and enzymes is applied to a stream of thin stillage and/or stream of whole stillage or a container of said stillage at desirable operating conditions suitable for propagation or action of the microorganism and enzyme chosen so as to facilitate the metabolizing of the stillage. The microorganism and enzyme act upon the thin or whole stillage to metabolize the stillage and more specifically carbohydrates, proteins, lipids and waxes, or gums, in the stillage. The present invention may also act upon and release at least a portion of the bound oil in distillers grains by microbial hydrolysis of proteins and polysaccharides in the germ. As a result of the foregoing, oil is released as free oil that otherwise cannot be separated by centrifugation and significant amounts of carbohydrates are converted into organic acids. Upon the action of the microorganism and enzyme, an emulsion is broken, resulting in free oils and the stillage liquid. The free oil may include oil already present in the stillage, as well as oil that has become un-bound or released or otherwise free due to the metabolism of proteins by the microbes and action of enzymes.

Figure 2:
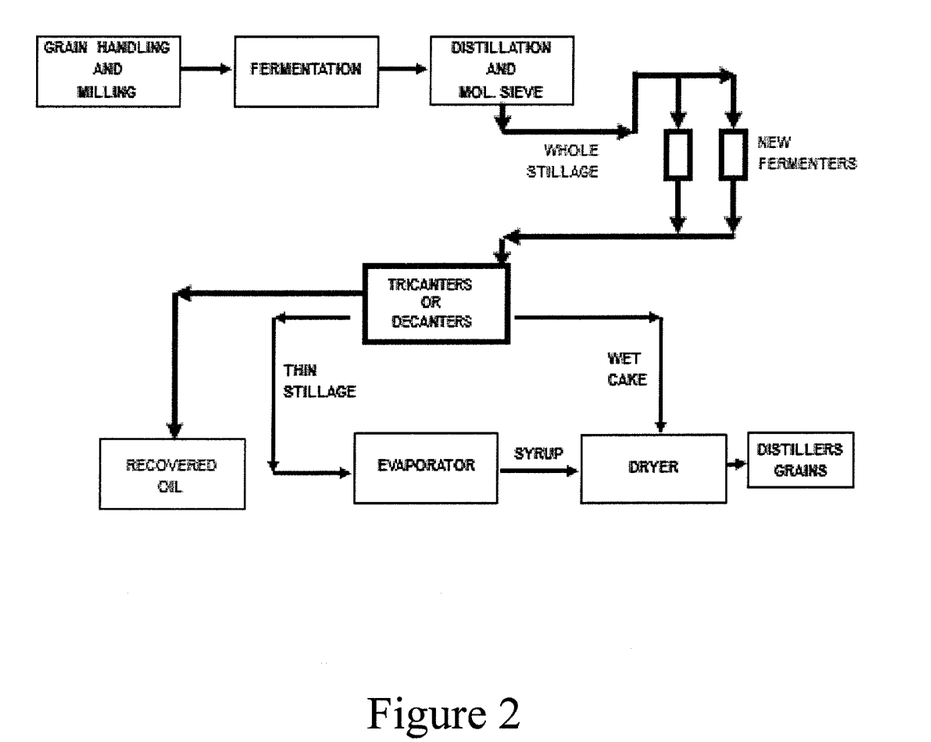
FIG. 2 shows a schematic diagram of a process flow in a dry mill ethanol plant after incorporation of the present invention to produce improved distillers grains.

One or more microorganisms and/or one or more enzymes are preferably added to whole stillage leaving the distillation column (see FIG. 2). Alternately, the microorganisms and/or enzymes can be added to thin stillage after separating the grains. Further, as discussed herein, the enzyme may be added by the action, that is, byproduct, of a particular microorganism, or may be added as a separate component of the mixture. Fermentation vessels may be preferably used for the fermentation of stillage including said microorganisms and/or enzymes. Preferably, the stillage will be fermented by batch culture, but continuous flow or continuous batch are also possible.

In a preferred embodiment of the method, the microorganisms (and/or enzymes where applicable) can be added directly to the stillage or propagated in seed cultures prior to inoculation of the stillage. The inoculation rate is preferably between $1\times10^3$-$1\times10^{15}$ colony forming units (cfu) per gram of stillage and more preferably between $1\times10^6$-$1\times10^{12}$ colony forming units per gram of stillage. A seed culture may be comprised wholly of stillage or any percentage of stillage. As indicated, the fermentation of stillage can occur by batch type, continuous flow, fed batch or any type of fermentation process. pH may be maintained in a range suitable for viability of the particular microorganism chosen. Culture temperature may be adjusted to meet the optimum temperature or temperature range for any given microorganism. Culture temperature is preferably between 20-60° C. and more preferably between 25-45° C. Culture time can vary and is optimum at such point when the gums have been sufficiently metabolized by the microorganism(s) to allow for efficient removal of the crude oil from the gum. Culture time is preferably between 6-120 hours and more preferably between 12 and 48 hours.

The inoculum may also optionally be added in hydrated form. The inoculum is preferably hydrated by adding dried microbes to water and either adding directly to the main culture or propagating the microbes first in a seed culture or series of seed cultures. Seed culture propagation can substantially reduce main culture fermentation time by effectively increasing the inoculation rate. Seed cultures, as described above, may be comprised of whole or thin stillage obtained from the production process. Micronutrients such as magnesium, manganese, zinc, selenium and vitamins can also be optionally added to seed cultures and the main culture.

The free or un-bound oil in the stillage, both present in the stillage and separated, removed, or otherwise un-bound by the action of the microorganism and/or enzyme, can be separated by centrifugation or simple decantation, and preferably centrifugation at lower speeds than traditionally required. In a preferred embodiment, the force used to separate the free "crude" oil via centrifugation can range from 500-10,000×g. More preferably, the force used may be between 1,000-5,000×g. In one further example, as shown in FIG. 2, at the completion of fermentation of stillage with the microorganism and/or enzyme, the stillage may be sent to or through a tricanter for separation of oil, solubles and wet cake streams in one pass, from the media. Following centrifugation, the separated oil may be removed or recovered by known means. The remaining thin stillage, after oil removal, may be sent, for example, to a steam evaporator to condense it to a syrup which can be sold, as is, or may be added to the grains to produce distillers grains plus solubles. The grains from the process can be sold and used wet or dry and with or without the solubles added.

In one embodiment, the grains will contain a reduced oil content compared with conventional distillers grains which contain from about 10 to about 15% oil. Preferably, the oil content of the process distillers grains will range from about 1% to about 8%, more preferably from about 1.5% to about 6% and even more preferably from about 2% to about 4.5% oil on a dry weight basis.

In a further embodiment, the distillers grains produced with the current process will contain a high organic acid content compared with conventional distillers grains which contain from about 0% to about 4% organic acids. Preferably the organic acid content of the present distillers grains will range from about 2% to about 30%, more preferably from about 4% to about 25% and even more preferably from about 5% to about 20% on a dry weight basis. The organic acids may include one or more of lactic, acetic, propionic, butyric, iso-butyric, valeric, iso-valeric, succinic, citric, malic, fumaric, aspartic and others or their equivalents.

The thin stillage may be sent to a steam evaporator to remove water and condense it to the byproduct condensed distillers solubles. Condensed distillers solubles can be sold, as is, or added back to the distillers grains and sold as distillers grains with solubles, either wet or dried. The coarse solids separated from the thin stillage by centrifuge may be processed or sold as wet distillers grains. The coarse solids may be dried using, for example, a rotary dryer (see FIG. 1), to form dried distillers grains.

Microorganisms suitable for use with the method of liberating bound oil include microbes or microorganisms which propagate in stillage and utilize compounds found in said stillage as a source of metabolizable carbohydrate. The microorganisms also may produce enzymes such as, but not limited to, proteases, cellulases and hemicellulases that act extracellularly to hydrolyze proteins and polysaccharides in stillage (which may bind oil as well, thus releasing more oil into the free oil form). The microorganisms may be aerobic, anaerobic or facultative or one or more combinations thereof. The microorganisms may, more preferably be bacterial.

In a preferred embodiment, the microbes chosen will liberate oil and produce a specific organic acid targeted for a specific feeding application. Published research has shown that increasing lactic acid in corn silage 2.5 times resulted in 7% faster weight gain and 5% improvement in feed efficiency in fattening beef steers (Klosterman, E. W. 1961. Feeding value for fattening cattle of corn silages treated to increase their content of organic acids. J. Anim. Sci. 20:493-496). Dairy cows fed barley steeped in lactic acid produced 34% more milk fat (Iqbal, S. et. al. 2009. Feeding barley grain steeped in lactic acid modulates rumen fermentation patterns and increases milk fat content in dairy cows. J. Dairy Sci. 92:6023-6032). Malic acid has been shown to reduce methane accumulation in simulated rumen digestions studies, which would lead to improvements in feed efficiency and digestible energy in cattle, similar to effects of feeding antibiotic ionophores (Martin, S. A. 1998. Manipulation of ruminal fermentation with organic acids: a review. J. Anim. Sci. 76:3123-3132). Pigs fed diets containing 1.8% formic acid had a 3% increase in feed efficiency compared with those fed a control diet without added acid (Eisemann, J. H. and Heugten, E. 2007. Response of pigs to dietary inclusion of formic acid and ammonium formate. J. Anim. Sci. 85:1530-1539). Dairy cows given feed with added propionic acid produced more milk fat compared with those receiving a control diet (DeFrain, J. M. et. al. 2005. Effects of feeding propionate and calcium salts of long-chain fatty acids on transition dairy cow performance. J. Dairy Sci. 88:983-993). Propionic acid is a glucogenic acid in ruminants and is used to produce glucose for use as a metabolic energy supply.

In another preferred embodiment, no additional nutrients are utilized for fermentation of whole stillage or thin stillage. The preferred microorganisms will propagate quickly using only the inherent nutrients within a stillage stream, thereby reducing costs while improving the nutrient content of the stillage used for livestock feed.

Microorganisms, such as bacteria, capable of propagating in stillage may be acceptable for the purposes provided. More preferably, the bacteria may be from the Class: Bacilli. Even more preferably, the bacteria may be from the Order: Lactobacillales, and even more preferably, the bacteria may be from the Genus: *Pediococcus, Lactobacillus, Enterococcus* or *Bacillus*. The bacteria may be further from the Genus: *Lactobacillus*; and Species: *Plantarum, Casei*, or *Acidophilus*. In other embodiments, the bacterial may from the Family: Enterobacteriaceae, Propionibacteriaceae, Pseudomonadaceae, or Acetobacteraceae. Further, the bacteria may be from the Genus: *Eschichia, Propionibacterium*, or *Acetobacter*. Further, the bacteria may be from the Specie: *coli* or *acidipropionci*. Such bacterial cultures are well known in the art, and are readily obtainable from conventional sources. Suitable microorganisms can be obtained or sourced from current commercial sources, such as Medipharm USA (Des Moines, Iowa), or may be obtained from a recognized depository such as the American Type Culture Collection (ATCC—Rockville, Md.) and various other sources known in the art. In yet another embodiment of the present invention, the bacteria may be genetically engineered to produce a particular metabolite in higher quantities. The foregoing organisms may be used alone or in any combination, and may further be used with one or several other microbes and/or enzymes, such as but not limited to alternative enzymes or microorganisms having different properties or purposes. While specific microorganisms are described, one of skill in the art would understand that alternative microorganisms or their equivalents suitable for accomplishing the purposes provided may be acceptable for use in the method described herein.

Enzymes suitable for use in one or more examples of embodiments may include, but are not limited to, beta-gulcanase, cellulases, hemicellulases, amylases, proteases, lipases or maltases, or combinations thereof. Suitable enzymes can be obtained or sourced from current commercial sources, such as AB Technologies (Springfield, Oreg.). The enzyme used may be purified or contained within a crude media, such as, but not limited to, the media in which a microbe that produced the enzyme was propagated in, or may alternatively be a separate component added to the mixture or to the stillage. As indicated, an enzyme can be used alone or in combination with other enzymes, including those enzymes listed herein or enzymes suitable for different purposes.

As described, the process of the present invention produces an improved livestock feedstuff as a byproduct of grain ethanol production, comprising reduced oil content and high content of energy dense organic acids. For example, propagation of microorganisms in stillage which are capable of metabolizing gums that form emulsions with oil while concomitantly creating organic acids results in a significant liberation of free oil that can be easily separated. Advantageously, a reduced oil distillers grains can be included into livestock diets at a higher inclusion level, thereby replacing more corn grain. Further, the high level of organic acids produced during the process, increases digestible energy content of the feedstuff and increases growth and production by livestock consuming the improved distillers grains.

The methods described herein improve the nutritional value and market demand of corn distillers grains byproduct by facilitating the recovery of crude oil from stillage and more efficiently reduce or extract the oil content of distillers grains byproduct, as well as produce significant amounts of energy dense organic acids, in a dry mill ethanol plant as compared to current systems. The improvement of the feeding value and demand of distillers grains, along with additional oil revenue, results in increased overall profitability of ethanol production plants, by reducing energy consumption and improving the value of byproducts. The production of energy dense organic acids increases the digestible energy content of distillers grains. In the method described and illustrated herein, the action of the microbes and/or enzymes upon the stillage results in an amount of free oil as well as the production of energy dense organic acids. The microorganisms advantageously utilize residual carbohydrates and proteins, thereby freeing oil, increasing cell biomass and producing energy dense organic acids such as, but not limited to, lactic, acetic, propionic, butyric, iso-butryic, valeric, iso-valeric, succinic, citric, malic, fumaric, aspartic, amino and others or their equivalents, as metabolic byproducts, in stillage. The method described provides further advantages, by removing the oil from the byproduct distillers grains, such as increasing the level of effective inclusion in livestock diets which permits the byproduct to be incorporated into livestock rations at higher levels, as well as allowing the oil to be directed toward higher value industrial processes or feed markets.

These and other advantages will be apparent from the foregoing description, Figures, the following Examples, and Claims.

EXAMPLES

The following Examples are an illustration of one or more examples of embodiments of carrying out the invention and are not intended as to limit the scope of the invention.

Example 1

Whole stillage was obtained from a corn to ethanol plant and used in a series of fermentations in four 11 L bioreactors. Treatments included four separate bacterial inoculants (A, B, C and D) along with an untreated control. The inoculation treatments were fermented in the bioreactors for 48 hours while the untreated control was processed without additional storage or agitation that would have mimicked residence time in a bioreactor. All treatments were replicated four times and fresh, whole stillage was obtained each morning of the fermentations. Upon arrival at the lab, whole stillage was pH adjusted to 6.5 using 50% KOH and then cooled to 35° C. using an immersion chiller. Bioreactors were charged with 7,600 grams of pH adjusted, whole stillage and subsequently inoculated with one of the four bacterial treatments. Inoculum was prepared freshly before use by adding 2 grams of dried inoculum containing $5 \times 10^9$ cfu per gram to 398 grams of di-ionized water and stirring well until suspended evenly. The bioreactors were then inoculated with the 400 g bacterial suspension to equal approximately $1.25 \times 10^6$ cfu per gram of whole stillage. The bioreactors were agitated continuously while also temperature (35° C.) and pH controlled (pH 6.5 using 50% KOH) during the duration of a 48 hour fermentation period. Treatments A, B, C and D consisted of *Lactobacillus casei, Pediococcus acidophilus, Lactobacillus plantarum*, and a mixture of these three along with added cellulose and protease, respectively. Bacteria inoculants and enzymes were all obtained from AB Technologies located in Springfield, Oreg.

At the conclusion of the fermentation period, the whole stillage ferment was processed as follows. A sample of each whole stillage ferment was frozen for later laboratory analyses. The whole stillage ferment was centrifuged in a swing basket centrifuge at 1,000×g for 5 minutes using 1,000 ml polypropylene bottles to separate heavy solids from solubles, oils and waxes. This low speed and centrifuging time were intended to simulate separation results that would be found in a commercial plant utilizing a decanter. After centrifuging, supernatents of each bottle within treatments were combined into an 11 L plastic bucket with a spigot fastened to bottom of the sidewall. The heavy solids remaining in each bottle were carefully removed, combined within each treatment and weighed. From each batch of heavy solids (wet cake) within treatments, three subsamples of approximately 150 g each was taken for dry matter determination (50° C. 48 hours) and sample retention. The oils and waxes were allowed to separate from the soubles in the 11 L bucket for at least 2 hours and no more than 5 hours before the soubles fraction was bottom decanted from each bucket using the spigot. The decanting was stopped just before the oil and wax layer reached the bottom. Retained was mostly oils and waxes with a small portion of the remaining soubles. This remainder was transfer to a 500 ml separatory funnel and the oils or waxes adhering to the sidewall were rinsed into the funnel with diethyl ether. After the oil and waxes separated from the soubles in the the separatory funnel, the soubles were bottom decanted more precisely and added to the previously separated solubles and a total weight was measured. The remaining oils and waxes were collected into 50 ml centrifuge tubes, all adhering to the sidewalls was rinsed out using diethyl ether. The collected oils and gums were then centrifuged lightly (1,000×g for 5 minutes) and the clear oil was decanted from the top into an additional tube. Both the waxes and the oils were then dried to evaporate ether before being weighed to record the amount of recoverable oil and waxes within treatment. Samples of the solubles were frozen for later lab analyses.

Samples of dried wet cake, frozen whole stillage and frozen solubles were sent to an outside laboratory (Dairyland Labs, Arcadia, Wis.) for chemical analyses. Ethanol soluble sugars were determined using 80% ethanol solution for extraction followed by a reaction with phenol-sulfuric acid and absorbance reading at 480 nanometers. Organic acids were determined using HPLC. Acid detergent and neutral fiber were determined by the VanSoest method.

Results are shown in Table 1. Treatment with each microorganism significantly increased recovery of oil by using very light centrifugation. In a commercial application, this would result in an additional and significant revenue stream from oil recovery and equally as important a lower oil distillers grains that can be fed at higher inclusion levels in livestock diets. Due to fermentation by microorganisms, soluble sugars significantly decreased compared with Control and most of the organic acids measure increased. Acid detergent fiber, a combination of mostly cellulose and lignin, actually increased after fermentation, probably due to some effect of concentration of nutrients. Neutral detergent fiber, including hemicellulose, cellulose and lignins, was largely unchanged.

Example 2

A trial was conducted to evaluate the two best performing microbial inoculants (oil recovery from whole stillage) from a previous trial either alone or in combination with or without additional enzymes and compared with control, un-fermented whole stillage for their effectiveness to ferment stillage and release oil for recovery. Treatments included Strain B (*Pediococcus acidophilus*), Strain C (*Lactobacillus plantarum*), Strain B+C, and Strain B+C+E (additional enzymes). Bacteria inoculants and enzymes were all obtained from AB Technologies located in Springfield, Oreg.

Two, five-liter bioreactors were used for the fermentations and treatments were assigned to each bioreactor so that no treatment was repeated within a bioreactor or day of fermentation (Table 2.). Each treatment was replicated twice during four fermentation periods for a total of eight fermentations. Whole stillage was obtained from Lincolnway Energy in Nevada, Iowa on the morning of each run. Sanitized containers were used to collect and transfer the stillage and care was taken to obtain a sample free of contaminants by emptying old stillage from sample ports before a sample of fresh material was collected. At the lab, the stillage was pH adjusted to 6.5 using potassium hydroxide. Three liters were subsampled, with care to maintain the material as homogenized as possible, and placed into one of two sanitized five-liter bioreactors. Immediately, the stillage was inoculated with 0.75 grams/3 L of either Strain B or Strain C, or 0.37 grams of Strain B and C each with our without 0.006 grams of additional enzymes. The enzymes used were mixture of proteases and cellulases with pH optima between 5 and 7. The treatments are shown in Table 1. The headspace of each bioreactor was gassed with nitrogen to achieve anaerobsis as quickly as possible. Fermentations lasted 48 hours. The temperature was maintained at 35 C and pH was maintained at 6.5 for the first 36 hours of fermentation with 0.5 molar potassium hydroxide and then allowed to drop for the final 12 hours. Samples of the stillage (c.a. 20 ml) were collected at 0, 21, 34 and 48 hours of fermentation and frozen for later lab analyses. Dissolved oxygen and pH were recorded during each fermentation using data loggers. At the end of each fermentation period, the bioreactors were opened and poured into large, sanitized, plastic beakers for sampling. Immediately, two 42 gram samples were collected into 50 ml centrifuge tubes for each treatment. In addition, approximately 500 mls from each was collected into sample bottles, preserved with sodium azide and frozen for later lab analyses. The 50 ml centrifuge tubes were centrifuged initially using 1,500 g for 5 minutes after which the free oil on top was diluted with hexane and decanted carefully before drying and weighing. The samples were centrifuged a second time using 3,000 g for 10 minutes and the free oil on top was again diluted with hexane and carefully decanted, dried and weighed. Finally the remaining solubles or supernatant was mixed with hexane and centrifuged a third time to release all remaining oil in the 'soluble phase' and the only remaining oil was that found in the pellet and bound to insoluble proteins. Separately, total oil in the whole stillage was determined as acid hydrolyzed oil. For each oil fraction; free oil1, free oil 2, hexane extracted oil and total acid hydrolyzed oil, fatty acids were determined. Total solids content of whole stillage, thin stillage and wet cake (fermented stillage, supernatant and pellet, respectively) was determined by weight loss in 60 C oven for 48 hours. Frozen samples collected during fermentation at 0, 21, 34 and 48 hours were used for analyses of citric acid, lactic acid, acetic acid, propionic acid and isobutyric acid by HPLC.

The results in Table 3 show the oil recovery was generally increased by 300% when whole stillage was fermented with microorganisms. Adding additional enzymes in this trial did not seem to have any affect upon additional oil removal. Organic acid concentration was increased dramatically during the fermentation period and lactic acid in particular reached a maximum concentration at about 21 hours. Enzyme additional did not seem to affect maximum organic concentration in this trial. The resulting feedstuff should have dramatically reduced oil content along with a high concentration of energy dense organic acids. The feedstuff so produced should be used at higher inclusion levels in livestock diets compared with higher-oil distillers grains and should support increased production of meat, milk or eggs per unit of feedstuff due to the concentration of energy into organic acids and an increased digestible energy content.

TABLE 1

Oil removal, organic acid production and fiber content of distillers feed produced.

| Item | Control | Trt-A | Trt-B | Trt-C | Trt-D | SEM[1] |
|---|---|---|---|---|---|---|
| Oil recovery, g/100 g solids | 0.40[a] | 2.28[b] | 2.79[b] | 2.13[b] | 1.88[ab] | 0.40 |

TABLE 1-continued

Oil removal, organic acid production and fiber content of distillers feed produced.

| Item | Control | Trt-A | Trt-B | Trt-C | Trt-D | SEM[1] |
|---|---|---|---|---|---|---|
| Ethanol soluble sugars, g/100 g solids | 16.53[q] | 6.80[qs] | 6.20[s] | 10.11[qs] | 5.81[s] | 2.63 |
| Lactic acid, g/100 g solids | 1.16 | 1.90 | 1.45 | 1.35 | 1.80 | |
| Acetic acid, g/100 g solids | 0.07 | 0.23 | 0.35 | 0.28 | .09 | |
| Propionic acid, g/100 g solids | 2.96 | 0.35 | 1.61 | 1.00 | .73 | |
| Isobutyric acid, g/100 g solids | .10 | 0.66 | 1.15 | 1.01 | 1.44 | |
| ADF[2] | 12.03[a] | 15.46 | 15.12[b] | 14.34[ab] | 14.36[ab] | 0.62 |
| NDF[3] | 28.20 | 32.12 | 31.61 | 30.92 | 30.81 | 0.45 |

[1]SEM—standard error of mean differences
[2]Acid Detergent Fiber
[3]Neutral Detergent Fiber
[ab]Means within rows with unlike superscripts differ. $P < 0.05$.
[qs]Means within rows with unlike superscripts differ. $P < 0.10$.

TABLE 2

Treatments assigned by run and by bioreactor.

| Run | Date | Bioreacter A | Bioreacter B |
|---|---|---|---|
| 1 | Jul. 14, 2010 | Trt-B | Trt-C |
| 2 | Jul. 27, 2010 | Trt-B + C | Trt B + C + Enzyme |
| 3 | Aug. 3, 2010 | Trt-C | Trt-B |
| 4 | Oct. 6, 2010 | TrtB + C + Enzyme | Trt-B + C |

TABLE 3

Oil recovery from fermentations. g/3L.

| | Treatments | | | |
|---|---|---|---|---|
| | Control | Trt-B | Trt-C | Trt B + C + E |
| Free oil 1 (1500 g, 5 min) | 3.61 | 11.70 | 16.51 | 13.03 |
| Free oil 2 (3000 g, 10 min) | 3.03 | 3.36 | 3.34 | 5.76 |
| Hexane-extractable oil | 11.56 | 6.75 | 8.95 | 10.82 |

TABLE 4

Organic Acid Production. mg/ml.

| | Lactic acid | | | Acetic acid | | | Iso-butyric acid | | |
|---|---|---|---|---|---|---|---|---|---|
| Time | Trt-B | Trt-C | Trt B + C + E | Trt-B | Trt-C | Trt B + C + E | Trt-B | Trt-C | Trt B + C + E |
| 0 hrs Control | 1.15 | 1.15 | 1.15 | 0.07 | 0.07 | 0.07 | 0.03 | 0.03 | 0.03 |
| 21 hrs | 42.41 | 26.77 | 24.35 | 1.24 | 0.87 | 1.86 | 3.72 | 4.66 | 4.49 |
| 34 hrs | 17.97 | 22.04 | 27.36 | 0.94 | 1.22 | 3.04 | 3.63 | 5.29 | 7.94 |
| 48 hrs | 18.43 | 19.34 | 27.26 | 1.28 | 1.66 | 3.64 | 3.89 | 5.52 | 5.44 |

Presently preferred embodiments of the invention and many of its improvements have been described with a degree of particularity. The previous description is of preferred examples for implementing the invention, and the scope of the invention should not necessarily be limited by this description. Although various representative embodiments of this invention have been described above with a certain degree of particularity, those skilled in the art could make numerous alterations to the disclosed embodiments without departing from the spirit or scope of the inventive subject matter set forth in the specification and claims. Any and all directional references (e.g., upper, lower, upward, downward, left, right, leftward, rightward, top, bottom, above, below, vertical, horizontal, angled, and so forth) are only used for identification purposes to aid the reader's understanding of the embodiments of the present invention, and do not create limitations, particularly as to the position, orientation, or use of the invention unless specifically set forth in the claims. Any and all joinder references (e.g., attached, coupled, connected, and the like) are to be construed broadly. As such, joinder references do not necessarily infer that two elements are directly connected and in fixed relation to each other.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It is also important to note that the methods, construction and/or arrangement as described in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements described as integrally formed may be formed of multiple parts or elements shown as multiple parts may be integrally formed, the interfaces may be reversed or otherwise varied, the length or width of the structures and/or members or other elements of the product or composition may be varied, the nature or number of adjustment positions provided between the elements may be varied. The order or sequence of any process or method steps may be varied or re-sequenced according to alternative embodiments. Other substitutions, modifications, changes and omissions may be made in the design, operating conditions and arrangement of the various exemplary embodiments without departing from the spirit or scope of the present inventions.

The invention claimed is:

1. A method for producing an improved distillers grains resulting from an ethanol production process comprising obtaining whole stillage, applying a mixture of microorganisms from the class Bacilli to the whole stillage in a fermentation process which application of microorganisms metabolizes the carbohydrates in the whole stillage with concomitant production of organic acids and reduction of oil by de-mulsification and liberation of oil for recovery, and separating the oil, whereby resultant distillers grains produced from the whole stillage have a reduced oil content and a concentration of energy dense organic acids.

2. The method of claim 1, wherein the ethanol production process is a dry-milling ethanol production process.

3. The method of claim 1, wherein the mixture of microorganisms is applied to by-product whole stillage resulting from the production of ethanol from grains in dry-milling ethanol.

4. The method of claim, wherein a microorganism is of the order Lactobacillales.

5. The method of claim 4, wherein the microorganism is selected from the group consisting of the genus *Pediococcus, Lactobacillus, Enterococcus* and *Bacillus*.

6. The method of claim 4, wherein the microorganism is selected from the group consisting of the species *Plantarum, Casei*, and *Acidophilus*.

7. The method of claim 1, wherein the mixture of microorganisms produces an enzyme selected from the group consisting of beta-glucanase, cellulases, hemicellulases, amylases, proteases, lipases and maltases.

8. The method of claim 1, wherein the organic acids produced comprise one or more of lactic, acetic, propionic, butyric, iso-butyric, valeric, iso-valeric, succinic, citric, malic, fumaric, aspartic, amino and others or their equivalents.

9. The method of claim 8, wherein the organic acids produced are selected from the group consisting of lactic, malic, fumaric and propionic acid.

10. The method of claim 1, wherein the organic acid concentration is equal to from about 2% to about 30% on a dry weight basis.

11. The method of claim 1, wherein the organic acid concentration is equal to from about 4% to about 25% on a dry weight basis.

12. The method of claim 1, wherein the organic acid concentration is equal to from about 5% to about 20% on a dry weight basis.

13. The method of claim 1, wherein the resultant distillers grains has an oil content from about 1% to 8% on a dry weight basis.

14. The method of claim 1, wherein the resultant distillers grains has an oil content from about 1.5% to about 6% on a dry weight basis.

15. The method of claim 1, wherein the resultant distillers grains has an oil content from about 2% to about 4.5% on a dry weight basis.

16. The method of claim 1, wherein the fermentation process is anaerobic.

17. The method of claim 1, wherein the fermentation process lasts from about 2 hours to about 60 hours.

18. The method of claim 1, wherein the fermentation process lasts from about 4 hours to 36 hours.

19. The method of claim 1, wherein the fermentation process lasts from about 6 hours to 24 hours.

* * * * *

UNITED STATES PATENT AND TRADEMARK OFFICE
CERTIFICATE OF CORRECTION

PATENT NO.        : 8,722,392 B2                                              Page 1 of 1
APPLICATION NO.   : 13/433099
DATED             : May 13, 2014
INVENTOR(S)       : Dale It is certified that error appears in the above-identified patent and that said Letters Patent is hereby corrected as shown below:

In the Specification

In Column 7, Line 34, delete "acidipropionci." and insert -- acidipropionici. --, therefor.

In Column 7, Lines 53-54, delete "beta-gulcanase," and insert -- beta-glucanase, --, therefor.

In Column 8, Line 31, delete "iso-butryic," and insert -- iso-butyric, --, therefor.

In Column 9, Line 31, delete "soubles in" and insert -- solubles in --, therefor.

In Column 9, Line 32, delete "soubles fraction" and insert -- solubles fraction --, therefor.

In Column 9, Line 37, delete "soubles." and insert -- solubles. --, therefor.

In Column 9, Line 37, delete "transfer" and insert -- transferred --, therefor.

In Column 9, Line 40, delete "in the the" and insert -- in the --, therefor.

In Column 9, Line 41, delete "soubles" and insert -- solubles --, therefor.

In the Claims

In Column 14, Line 18, in Claim 4, delete "claim," and insert -- claim 1, --, therefor.

In Column 14, Line 23, in Claim 6, delete "microoganism" and insert -- microorganism --, therefor.

Signed and Sealed this
Twentieth Day of January, 2015

Michelle K. Lee
*Deputy Director of the United States Patent and Trademark Office*